United States Patent
Kaneko (10) Patent No.: US 10,262,225 B2
(45) Date of Patent: Apr. 16, 2019

(54) IMAGE INFORMATION PROCESSING DEVICE, IMAGE INFORMATION PROCESSING SYSTEM, IMAGE INFORMATION PROCESSING METHOD, AND RECORDING MEDIUM STORING IMAGE INFORMATION PROCESSING PROGRAM

(71) Applicant: NEC Corporation, Minato-ku, Tokyo (JP)

(72) Inventor: Eiji Kaneko, Tokyo (JP)

(73) Assignee: NEC CORPORATION, Tokyo (JP)

(*) Notice: Subject to any disclaimer, the term of this patent is extended or adjusted under 35 U.S.C. 154(b) by 122 days.

(21) Appl. No.: 15/535,128

(22) PCT Filed: Dec. 17, 2015

(86) PCT No.: PCT/JP2015/006280
§ 371 (c)(1),
(2) Date: Jun. 12, 2017

(87) PCT Pub. No.: WO2016/098353
PCT Pub. Date: Jun. 23, 2016

(65) Prior Publication Data
US 2017/0344845 A1  Nov. 30, 2017

(30) Foreign Application Priority Data
Dec. 19, 2014 (JP) .............................. 2014-257039

(51) Int. Cl.
*G06T 1/00* (2006.01)
*G06K 9/40* (2006.01)
(Continued)

(52) U.S. Cl.
CPC ............... *G06K 9/40* (2013.01); *G01J 3/28* (2013.01); *G01N 21/27* (2013.01); *G06K 9/0063* (2013.01); *G06K 9/4661* (2013.01); *G06T 1/00* (2013.01)

(58) Field of Classification Search
CPC .................................... G06T 1/00; G06K 9/00
(Continued)

(56) References Cited

U.S. PATENT DOCUMENTS 9,128,055 B2 * 9/2015 Sekino ............... G01N 21/6408
2006/0126959 A1 * 6/2006 Padwick .............. G06K 9/0063
382/254
(Continued)

FOREIGN PATENT DOCUMENTS

JP  2013-225243 A  10/2013
JP  2015-036850 A   2/2015

OTHER PUBLICATIONS

Robert A Schowengerdt Ed, "Remote sensing: models and methods for image processing, Chapter 1: The Nature of Remote Sensing, Chapter 2: Optical Radiation Models, Chapter 7: Correction and Calibration", Dec. 31, 2007, Remote Sensing: Models and Methods for Image Sensing, Amsterdam, Elsevier Academic Press, NL, pp. 1-73, 285, 337-354, XP002558565 (161 pages total).
(Continued)

*Primary Examiner* — Abolfazl Tabatabai (57) ABSTRACT

In an image representing an observed ground surface area, the device calculates an optical-path-radiance with a high degree of accuracy. An image information processing device 3 includes: a storage unit 31 that associates and stores observation images representing the results of observing electromagnetic waves of a plurality of different wavelength bands reflected from a ground surface, information representing the wavelength bands, and information representing the observation environment; a first intermediate-optical-
(Continued)

path-radiance calculation unit that, for each of the wavelength band, makes the radiance of a dark pixel meeting a radiance standard from among pixels composing an associated observation image an intermediate-optical-path-radiance; an irradiance calculation unit that calculates the irradiance from sunlight for each of the wavelength band on the basis of the information representing the observation environment; and a final-optical-path-radiance calculation unit that calculates a final-optical-path-radiance for each of the wavelength band on the basis of the irradiance and intermediate-optical-path-radiance.

10 Claims, 7 Drawing Sheets

(51) Int. Cl.
*G01N 21/27* (2006.01)
*G01J 3/28* (2006.01)
*G06K 9/00* (2006.01)
*G06K 9/46* (2006.01)

(58) Field of Classification Search
USPC .......................................... 382/103; 348/169
See application file for complete search history.

(56) References Cited

U.S. PATENT DOCUMENTS

2010/0008595 A1   1/2010   Riley et al.
2014/0270332 A1   9/2014   Pacifici

OTHER PUBLICATIONS

Extended European Search Report dated Jul. 5, 2018 issued by the European Patent Office in counterpart application No. 15869562.7.
R. Bird et al., "Simple Solar Spectral Model for Direct and Diffuse Irradiance on Horizontal and Tilted Planes at the Earth's Surface for Cloudless Atmospheres", U.S. Department of Energy, No. DE-AC02-83CH10093, Dec. 1984.
Satoshi Tsuchida, "Practical series 2 of resources / environment remote sensing: processing of global observation data: atmosphere correction in the visible light region / infrared region" (P124-P139 Aug. 2002).
International Search Report for PCT Application No. PCT/JP2015/006280, dated Mar. 1, 2016.
English translation of Written opinion for PCT Application No. PCT/JP2015/006280.

\* cited by examiner

IMAGE INFORMATION PROCESSING DEVICE, IMAGE INFORMATION PROCESSING SYSTEM, IMAGE INFORMATION PROCESSING METHOD, AND RECORDING MEDIUM STORING IMAGE INFORMATION PROCESSING PROGRAM

This application is a National Stage Entry of PCT/JP2015/006280 filed on Dec. 17, 2015, which claims priority from Japanese Patent Application 2014-257039filed on Dec. 19, 2014, the contents of all of which are incorporated herein by reference, in their entirety.

TECHNICAL FIELD

The present invention relates to an image information processing device and the like which remove an environment fluctuation component from an observation image representing a result of observing an electromagnetic wave reflected from the ground surface.

BACKGROUND ART

An art of observing the ground surface from a height by an observation device, which is installed in a man-made satellite or an airplane, is called the remote sensing. In the remote sensing, there are many cases that intensity of the electromagnetic wave such as light or the like, which is emitted from an area having a predetermined size on the ground surface, is observed. Moreover, there are many cases that, regarding an observation result which is obtained by the remote sensing, an observation value is stored as pixel values of plural pixels composing an image (observation image). The pixel value is a value of a pixel which, in the observation image, is corresponding to a position according to an arrangement on the ground surface of the observed area. Particularly, in the case that the observation device is an image sensor, the observation result is generated as an image. A pixel value of a pixel, which is included by the image, is an observation value which is outputted by a light receiving element of the image sensor when the light receiving element receives intensity of observation light emitted in an incident direction of the light receiving element. Here, in the case that the pixel value is composed of at least a value which expresses radiance for each of observed wavelength bands, the value which expresses the radiance is also denoted as a radiance value. There are many cases that observation is carried out by using a filter which selectively transmits an electromagnetic wave having a wavelength within a wavelength band existing in a specified range. In this case, intensity of the electromagnetic wave, which is observed for each wavelength band, is obtained as the observation image by using a plurality of filters which have different wavelength bands for transmitting the electromagnetic wave.

As an application by which it is expected to utilize the observation image, farming support, resource exploration, or the like is exemplified. In order to realize the farming support, the resource exploration or the like with preciseness, it is necessary to obtain correct information on an object existing on the ground surface such as a farm product, an ore or the like. However, an observation value which is obtained as the observation image is influenced by radiance of illumination due to sunlight, absorption by the atmosphere and scattering by the atmosphere in addition to reflection from a surface of observation target. Therefore, the observation value is expressed by a formula which includes, in addition to the surface reflectance of an object corresponding to the observation target, the intensity of the illumination due to the sunlight, a component depending on the transmittance of the atmosphere's transmitting the electromagnetic wave, and a component of the electromagnetic wave which is scattered by the atmosphere and is inputted into the sensor. However, the intensity of the illumination due to the sunlight, the transmittance of the atmosphere, and the light scattered by the atmosphere are fluctuated by an environmental condition such as a fluctuation of an altitude of the sun, a fluctuation of a state of the atmosphere or the like. Therefore, in order to obtain accurate information on the object which exists on the ground surface, it is necessary to calculate an environment fluctuation component which does not depend on the object on the ground surface and remove the environment fluctuation component. Formula. 1 is a formula which expresses influence of the environment condition on the observed electromagnetic wave (observation light).

$$L(\lambda) = \alpha(\lambda) R(\lambda) + \beta(\lambda) \qquad \text{[Formula. 1]}$$

In Formula. 1, $L(\lambda)$ is a radiance value of the observation light for each wavelength $\lambda$. $R(\lambda)$ is the surface reflectance of the object which exists on the ground surface. As shown by Formula. 1, the environment fluctuation component is mainly classified into two components. That is, in the case that the surface reflectance of the object existing on the ground surface is denoted as $R(\lambda)$, one is a component $\alpha(\lambda)$ which is expressed as a coefficient of $R(\lambda)$, and the other is a component $\beta(\lambda)$ which is represented as an addition term to $\alpha(\lambda)R(\lambda)$. Out of the components, the coefficient component $\alpha(\lambda)$ is a component which relates to the intensity of illumination due to the sunlight and the transmittance of the electromagnetic wave which is transmitted by the atmosphere. The addition term component $\beta(\lambda)$ expressed as an additional term is a component which is the observation light reaching the image sensor with no reflection from the object existing on the ground surface like the sunlight scattered by the atmosphere, and which expresses an optical path radiance. The relation shown by Formula. 1 is satisfied by an observation value which is observed in any wavelength band.

Figure 5:
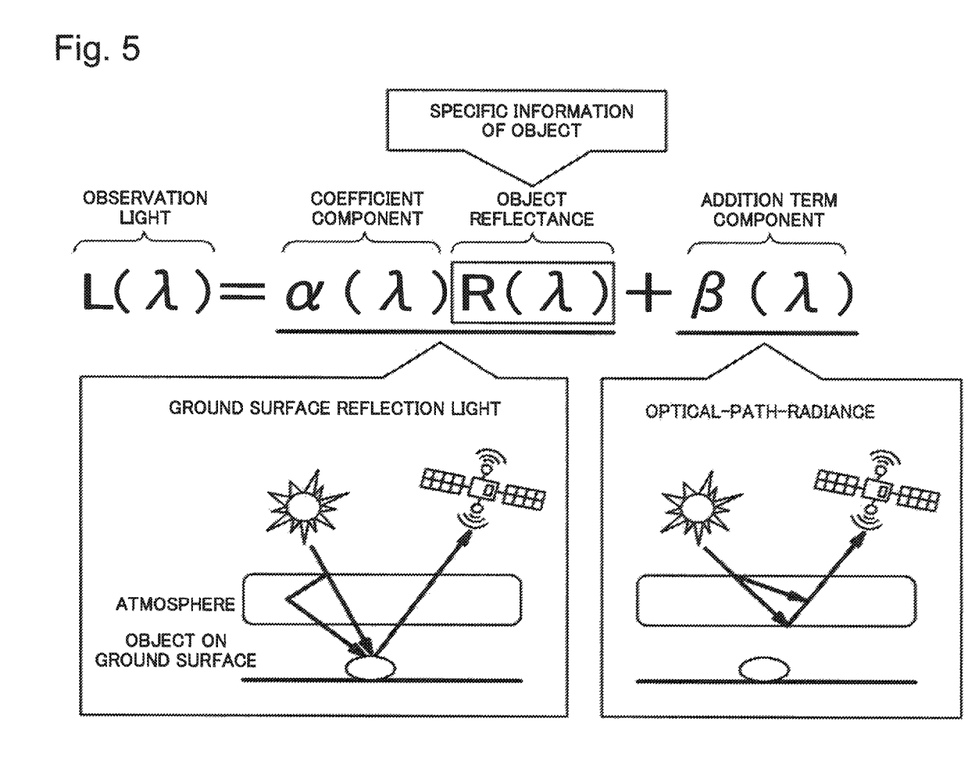
FIG. 5 is a diagram showing a relation between observation light and an environment fluctuation component in an image which is photographed at a height.

FIG. 5 is a diagram showing a relation between the observation light and the environment fluctuation component (environment noise), which is expressed as the coefficient term component and the addition term component, in the image which is photographed at the height. As shown in FIG. 5, the radiance value $L(\lambda)$ of the observation light is a value which is obtained by multiplying the surface reflectance $R(\lambda)$ of the object existing on the ground surface by the coefficient component $\alpha(\lambda)$, and adding the addition term component $\beta(\lambda)$ (optical path radiance) to the component (reflection light reflected from the ground surface) which is corresponding to the multiplication result.

As mentioned above, in order to obtain the correct information on the object existing on the ground surface, it is necessary to calculate the environment fluctuation component which does not depend on the object existing on the ground surface, and afterward to remove the environment component from the observation light. Therefore, there is increasing expectation for an art of calculating the environment fluctuation component with a high degree of accuracy.

As an example of the above-mentioned art, PTL 1 discloses an image processing device which calculates an optical path radiance on the basis of the observation image including the optical path radiance, and corrects the optical path radiance by using the optical path radiance which is calculated on the basis of the observation image. The image processing device makes the minimum pixel value $L(\gamma)$ out of the observation image in a wavelength band $\gamma$ a calculation value of the optical path radiance.

Figure 6:
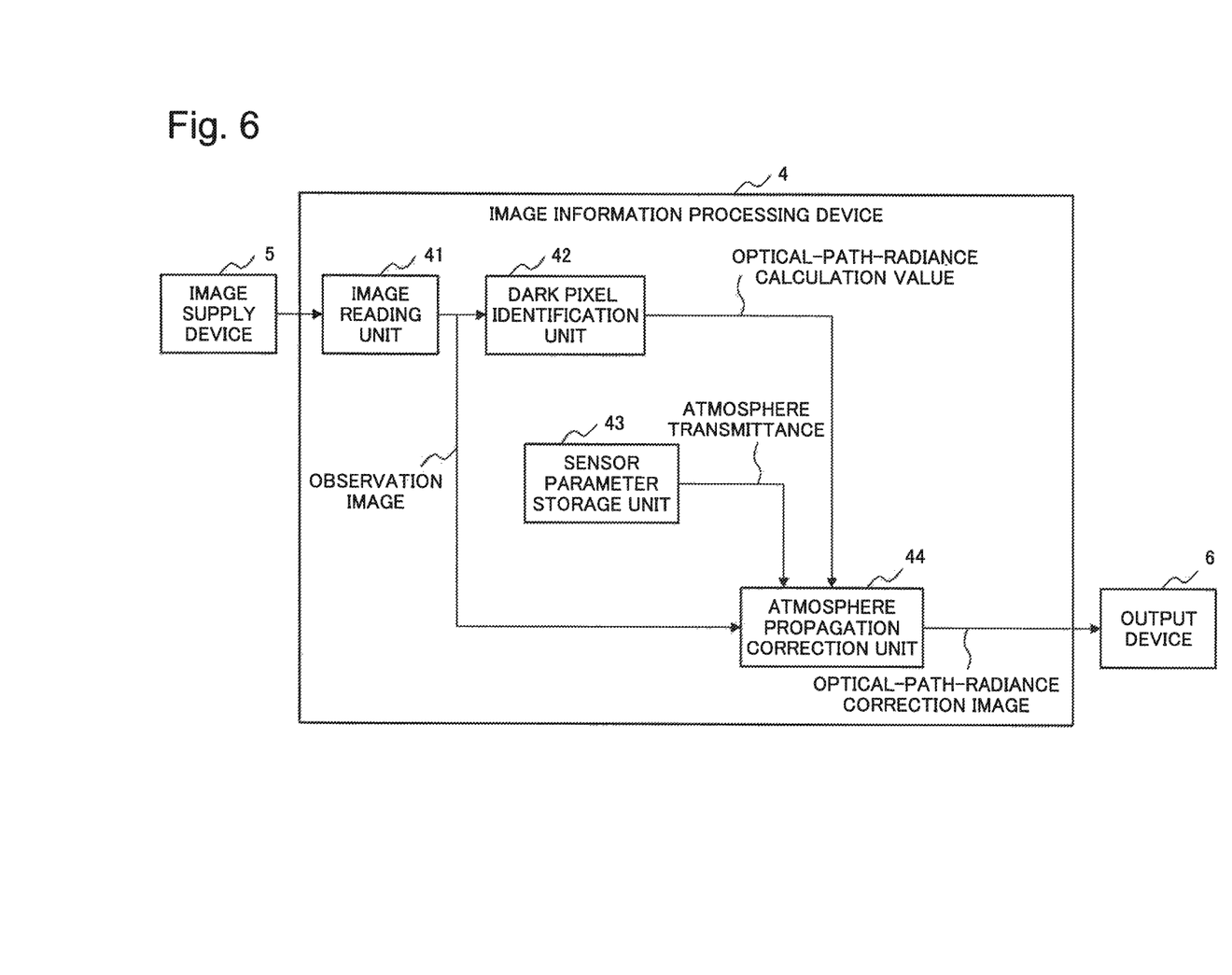
FIG. 6 is a block diagram showing a configuration of an image information processing device which uses an art disclosed by PTL 1.

FIG. 6 is a block diagram showing a configuration of an image information processing device 4 which uses the art disclosed by PTL 1. The image information processing device 4 includes an image reading unit 41, a dark pixel identification unit 42, a sensor parameter storage unit 43 and an atmosphere propagation correction unit 44. The image reading unit 41 reads the observation image from an image supply device 5. The dark pixel identification unit 42 extracts the minimum pixel value out of the inputted observation image for each wavelength band $\gamma$. The dark pixel identification unit 42 makes the smallest pixel value, which is extracted for each wavelength band $\gamma$, a calculation value $\beta^W(\gamma)$ of the optical path radiance. The sensor parameter storage unit 43 stores an atmosphere transmittance $\tau(\gamma)$ in each wavelength band. The atmosphere propagation correction unit 44 subtracts the calculation value $\beta^W(\gamma)$ of the optical path radiance in each wavelength band $\gamma$ from the radiance value $L(\gamma)$ for all pixels of the observation image.

Then, the atmosphere propagation correction unit 44 generates an optical path radiance correction image by dividing the subtraction result by the atmosphere transmittance $\tau(\gamma)$, which is stored by the sensor parameter storage unit 43, in each wavelength band $\gamma$. The atmosphere propagation correction unit 44 outputs the generated optical path radiance correction image to an output device 6.

CITATION LIST

Patent Literature

[Patent Literature 1] Japanese Patent Application Laid-Open Publication No. 2013-225243

Non Patent Literature

[Non Patent Literature 1] "Simple Solar Spectral Model for Direct and Diffuse Irradiance on Horizontal and Tilted Planes at the Earth's Surface for Cloudless Atmospheres", R. E. Bird, C. Riordan. (December 1984)

[Non Patent Literature 2] "Practical series 2 of resources/environment remote sensing: processing of global observation data: atmosphere correction in the visible light region/infrared region" Satoshi TSUCHIDA (P124-P139 August 2002)

SUMMARY OF INVENTION

Technical Problem

The image processing device which uses the art described by PTL 1 makes the minimum radiance value out of the observation image in the wavelength band $\gamma$ the calculation value of the optical path radiance. However, it is necessary to satisfy a specific condition in order to realize that the optical path radiance becomes the minimum radiance value out of the observation image in the wavelength band $\gamma$. The specific condition is that, in a ground surface area which is observed as an image, the surface reflectance of a dark area, which is corresponding to the pixel having the minimum radiance, can be considered to be 0 (zero) in the wavelength band $\gamma$. In the case that the condition is not satisfied, the radiance value includes a component of the surface reflection light even in the dark area. As a result, in the case of the image processing device which is described by PTL 1, it is impossible to correctly calculate the optical path radiance.

That is, it is a current problem to correctly calculate the optical path radiance even in the wavelength band in which the surface reflectance of the dark area cannot be considered to be 0. A main object of the present invention is to provide an image information processing device which solves the above-mentioned problem.

Solution to Problem

An image information processing device according to an aspect of the invention of the present application includes: a storage unit in which observation images representing results of observing electromagnetic waves of a plurality of different wavelength bands reflected from a ground surface, information representing the wavelength bands, and information representing an observation environment, which the electromagnetic waves are observed, are associated and stored; a first intermediate-optical-path-radiance calculation unit that, for each of the wavelength band, calculates radiance of a dark pixel meeting a radiance standard from among pixels composing the observation image, which is associated with the wavelength band, as a first intermediate-optical-path-radiance; an irradiance calculation unit that calculates, for each of the wavelength band, irradiance from sunlight on the basis of the information representing the observation environment; and a final-optical-path-radiance calculation unit that calculates, for each of the wavelength band, a final-optical-path-radiance on the basis of the irradiance and the first intermediate-optical-path-radiance.

From another point of view for achieving the above-mentioned object, an image information processing method according to an aspect of the invention of the present application includes: in a case that observation images representing results of observing electromagnetic waves of a plurality of different wavelength bands reflected from a ground surface, information representing the wavelength bands, and information representing an observation environment in which the electromagnetic waves are observed are associated and stored in a storage means, by an information processing device: calculating, for each of the wavelength band, radiance of a dark pixel meeting a radiance standard from among pixels composing the observation image which is associated with the wavelength band, as a first intermediate-optical-path-radiance; calculating, for each of the wavelength band, irradiance from sunlight on the basis of the information representing the observation environment; and calculating, for each of the wavelength band, a final-optical-path-radiance on the basis of the irradiance and the first intermediate-optical-path-radiance.

From furthermore another point of view for achieving the above-mentioned object, an image information processing program according to an aspect of the invention of the present application makes a computer, which is capable of accessing a storage means in which observation images representing results of observing electromagnetic waves of a plurality of different wavelength bands reflected from a ground surface, information representing the wavelength bands, and information representing an observation environment in which the electromagnetic waves are observed are associated and stored, carry out following processing: an intermediate-optical-path-radiance calculation processing of calculating, for each of the wavelength band, radiance of a dark pixel meeting a radiance standard from among pixels composing the observation image which is associated with the wavelength band, as a first intermediate-optical-path-radiance; an irradiance calculation processing of calculating, for each of the wavelength band, irradiance from sunlight on the basis of the information representing the observation environment; and a final-optical-path-radiance calculation processing of calculating, for each of the wavelength band, a final-optical-path-radiance on the basis of the irradiance and the first intermediate-optical-path-radiance.

Furthermore, the present invention can be realized also by a computer-readable and non-volatile recording medium which stores the image information processing program (computer program).

Advantageous Effect of Invention

According to the invention of the present application, it is possible to calculate the optical path radiance with a high degree of accuracy even in the wavelength band in which the surface reflectance of the dark area in the image representing the observed ground surface cannot be considered to be 0.

DESCRIPTION OF EMBODIMENTS

Hereinafter, an example embodiment of the invention of the present application will be explained in detail with reference to drawings.

<First Example Embodiment>

Figure 1:
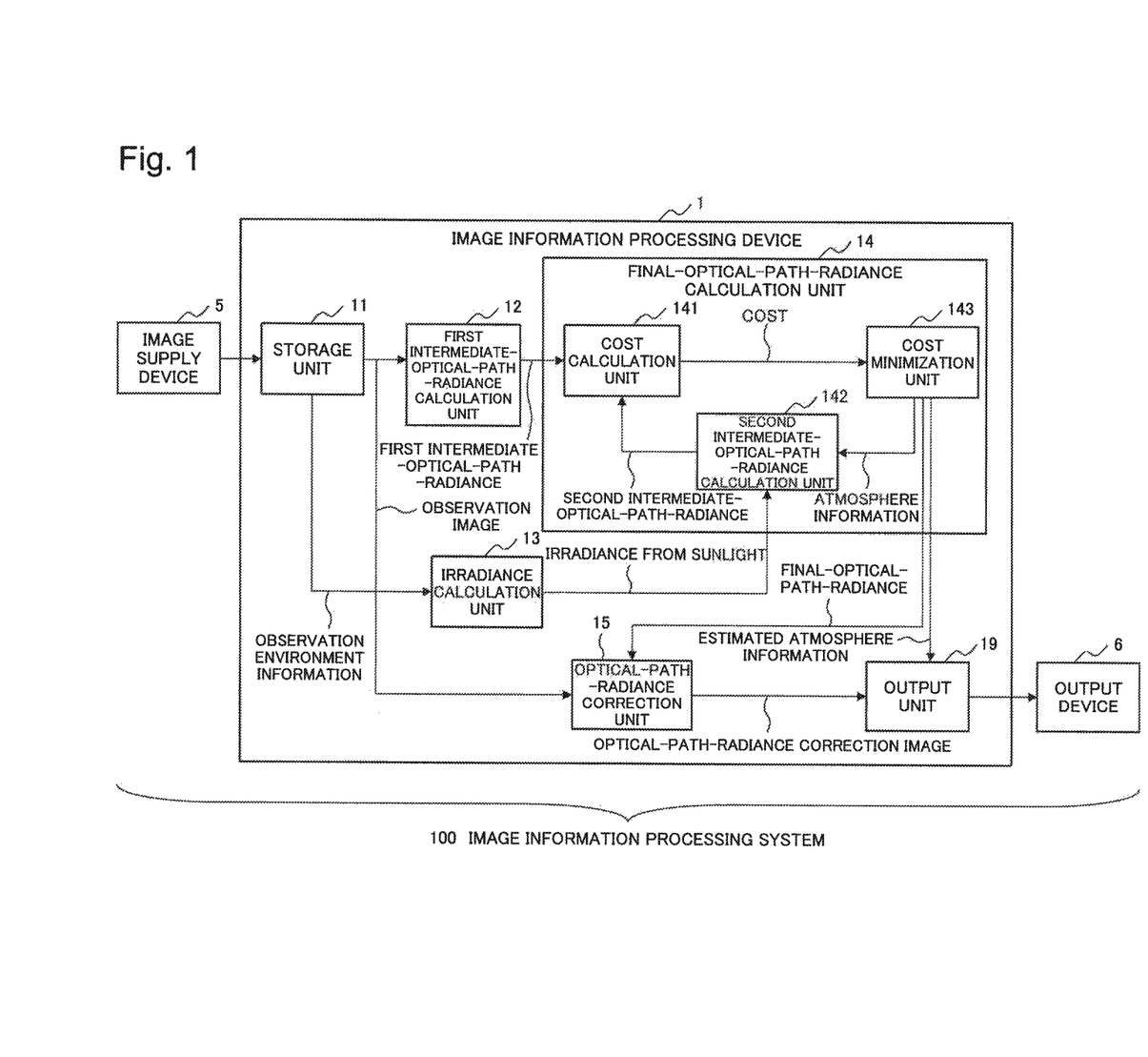
FIG. 1 is a block diagram showing a configuration of an image information processing system according to a first example embodiment of the invention of the present application.

FIG. 1 is a block diagram showing an image information processing system 100 of a first example embodiment of the present invention. The image information processing system 100 according to the present example embodiment includes an image information processing device 1, an image supply device 5 and an output device 6 as a main block. The image information processing device 1 is connected with the image supply device 5 and the output device 6 so as to be able to communicate each other. Here, a direction of arrow, which is described in the block diagram such as FIG. 1 and the like is according to the present application is merely exemplified, and the direction does not limit a direction of signal between the blocks.

The image supply device 5 is, for example, a photographing device which, for each of the plural wavelength bands different each other, observes intensity of an electromagnetic wave (observation light) reflected from an observation target, and outputs the observation result as an observation image. Or, the image supply device 5 may be a storage device such as a hard disk or the like, or an information processing device such as a server device or the like which stores the observation image corresponding to the observation result outputted by the photographing device. In the following explanation, N (N is an integer larger than 1) is number of wavelength bands which are used when the image supply device 5 (photographing device) observes the observation object.

The image supply device 5 supplies the image information processing device 1 with the observation images whose number is N and each of which is associated with the corresponding wavelength band. The Image supply device 5 may supply the image information processing device 1 with N observation images, and the maximum value and the minimum value of the wavelength band which is associated with each observation image. Moreover, the image supply device 5 supplies the image information processing device 1 with information which expresses an observation environment existing at a time of observation. The information which expresses the observation environment includes, for example, altitude of the sun at a time of observation, an observation date, observation time, latitude and longitude of an observation target area, topography of the observation target area, quantity of steam and quantity of aerosol in the observation target area, or the like.

The Image supply device 5 observes distribution of intensity of observation light which is emitted by the observation target to reach the image supply device 5 through a medium such as the atmosphere, dust or the like. In each example embodiment of the invention of the present application, the observation light includes visible light, infrared rays and ultraviolet rays. However, the image supply device 5 may observe distribution of intensity of an electromagnetic wave other than the visible light, the infrared rays and the ultraviolet rays.

As will be mentioned later, the observation light which reaches the image supply device 5 includes a component which reaches through the medium in addition to a component which reaches by reflection at the observation target. The observation target is, for example, the ground surface. The image supply device 5 is installed, for example, on an airplane or a man-made satellite. Then, by making a plurality of wavelength bands, which are different each other, the observation target, the image supply device 5 observes reflection light, which is reflected from the ground surface, in the air as a part of the observation light. The image supply device 5 is, for example, a camera which photographs through a band-pass filter. The image supply device 5 may carry out observation by using N band-pass filters each of which selectively transmits any one of N different wavelength bands. Here, in place of observing the ground surface in the air, the image supply device 5 may observe the distant ground surface from the ground surface or a near place above the ground surface. The wavelength bandwidth may not be uniform. The image supply device 5 outputs the observation result as N observation images.

Each of N observation images is an image which is generated by observing any one of N different wavelength bands and which expresses distribution of radiance related to the observation target. In each observation image, the radiance value of each pixel expresses intensity of the observation light which reaches from a direction according to the pixel. The above-mentioned N observation images are images which are obtained by observing the same observation target. In this case, N images are, for example, results which are obtained by the image supplying device 5's observing the observation target by using N wavelength bands. Moreover, in the case that a value of the optical path radiance is the same or almost the same in all observation areas of each image, the above-mentioned N images may be images which are obtained by observing the different observation targets. In this case, a manager who manages, for example, the image supply device 5 or the image information processing device 1 may select N images.

The output device 6 is, for example, a display unit. Moreover, the output device 6 may be, for example, an object identification device or the like which extracts information on a material or a state of the photographing object from the observation image.

The image information processing device 1 includes a storage unit 11, a first intermediate-optical-path-radiance calculation unit 12, an irradiance calculation unit 13, a final-optical-path-radiance calculation unit 14, an optical-path-radiance correction unit 15, and an output unit 19. The storage unit 11 is a storage device such as a magnetic disk, an electronic memory or the like. There is a case that the first intermediate-optical-path-radiance calculation unit 12, the irradiance calculation unit 13, the final-optical-path-radiance calculation unit 14, the optical-path-radiance correction unit 15, and the output unit 19 are realized by using electronic circuits, and there is another case that they are realized by using a computer program and a processor which works according to the computer program.

The storage unit 11 reads N observation images, which are associated with the observed wavelength bands respectively, from the image supply device 5. The storage unit 11 associates the read N observation images with the wavelength bands by which the observation images are observed, and stores the read N observation images. The wavelength band which is associated with the observation image may be, for example, a combination of the minimum value and the maximum value of the wavelength which indicate the wavelength band. The wavelength band which is associated with the observation image may be an identifier assigned to the combination of the minimum value and the maximum value of the wavelength which indicate the wavelength band. The storage unit 11 associates and stores the information representing the observation environment with the observation image. The information which expresses the observation environment includes, for example, altitude of the sun at a time of observation, an observation date, observation time, latitude and longitude of an observation target area, topography of the observation target area, quantity of steam, quantity of aerosol or the like at a time of observation.

The first intermediate-optical-path-radiance calculation unit 12 extracts a radiance value of the pixel, which meets a radiance standard, out of all pixels composing the observation images which are stored by the storage unit 11 and which are associated with N wavelength bands respectively. Then, the first intermediate-optical-path-radiance calculation unit 12 makes each of the extracted N radiance values the first intermediate-optical-path-radiance of each wavelength band. For example, the first intermediate-optical-path-radiance calculation unit 12 extracts the minimum radiance value as the radiance value which meets the radiance standard. Moreover, for example, in the case that the radiance values of all pixels are lined up in an order of smallness, the first intermediate-optical-path-radiance calculation unit 12 may extract the radiance value, whose rank in the line is coincident with number obtained by multiplying number of all pixels by a predetermined ratio, as the radiance value which meets the radiance standard.

In the following explanation, a pixel, which is corresponding to the radiance value extracted by the first intermediate-optical-path-radiance calculation unit 12, is referred to as 'dark pixel'. Moreover, an assumption that the surface reflectance of a dark area of the ground surface, which is measured as the radiance value of the dark pixel, can be considered to be 0 is referred to as 'dark pixel assumption'. Moreover, i'th (i is an integer of any one of 1 to N) wavelength band out of N wavelength bands, which are associated with N observation images respectively, is denoted as $\gamma_i$. Moreover, the extracted radiance value of the dark pixel in the wavelength band $\gamma_i$ out of N wavelength bands associated with the observation images is referred to as the first intermediate optical path radiance $\beta^D(\gamma_i)$.

The irradiance calculation unit 13 calculates the irradiance from the sunlight in the wavelength band $\gamma_i$ out of N wavelength bands on the basis of the information which expresses the observation environment and which is stored by the storage unit 11. In the following explanation, the irradiance from the sunlight, which is calculated by the irradiance calculation unit 13, in the wavelength band $\gamma_i$ out of N wavelength bands is denoted as $I(\gamma_i)$. For example, the irradiance calculation unit 13 calculates the irradiance $I(\gamma_i)$ by using a physical model shown by NPL 1 which expresses the irradiance. By using the physical model, the irradiance calculation unit 13 simulates direct sunlight and light, which is scattered by the atmosphere, by using parameters representing the zenith angle of sun, which is calculated on the basis of a location and time, and a state of the atmosphere. By virtue of the above, the irradiance calculation unit 13 can calculate, for example, the spectral irradiance of the sunlight, which is observed at a sunny time, for each wavelength.

In the case of using the physical model, firstly, the irradiance calculation unit 13 sets a predetermined value of the parameter which has a small amount of influence on the simulation result. Then, the irradiance calculation unit 13 calculates the spectral irradiance, which is irradiance per a unit wavelength of the sunlight at a sunny time, by using the predetermined value, and the zenith angle of sun and a value representing the state of atmosphere out of the information representing the observation environment. Then, the irradiance calculation unit 13 calculates a total amount of the spectral irradiance of the sunlight at the sunny time from the minimum value of the wavelength up to the maximum value of the wavelength out of the wavelength band $\gamma_i$. By carrying out the above, the irradiance calculation unit 13 calculates the irradiance $I(\gamma_i)$ for each wavelength band $\gamma_i$ out of N wavelength bands.

Moreover, the irradiance calculation unit 13 may stores the standard irradiance from the sunlight for each wavelength band $\gamma_i$ out of N wavelength bands, and may use the standard irradiance in place of the irradiance $I(\gamma_i)$. As shown, for example, by NPL2, the irradiance calculation unit 13 calculates a total amount of the spectral irradiance of the sunlight which is observed at a position where the sunlight enters into the inner space from the outer space, from the minimum value of the wavelength up to the maximum value of the wavelength out of the wavelength band $\gamma_i$. By carrying out the above, the irradiance calculation unit 13 may calculate and store the irradiance for each wavelength band $\gamma_i$ out of N wavelength bands.

The final-optical-path-radiance calculation unit 14 includes a cost calculation unit 141, a second intermediate-optical-path-radiance calculation unit 142, and a cost minimization unit 143.

The second intermediate-optical-path-radiance calculation unit 142 calculates a second intermediate-optical-path-radiance by using the irradiance $I(\gamma_i)$ which is calculated by the irradiance calculation unit 13, and atmosphere information which is outputted by the cost minimization unit 143. In the following explanation, a parameter out of M parameters representing the atmosphere information outputted by the cost minimization unit 143 is denoted as $X_j$ (j is an integer of any one of 1 to M and is a subscript for identifying the parameter.). The atmosphere information $X_j$ expresses information on a particle, which is included by the atmosphere, such as a molecule, aerosol, sand, soot, or the like. The atmosphere information $X_j$ is, for example, an angstrom index, atmosphere turbidity, atmosphere transmittance, an optical thickness of atmosphere molecule, an optical thickness of aerosol, visibility or a value which is calculated by using these. Moreover, the second intermediate-optical-path-radiance, which is calculated by the second intermediate-optical-path-radiance calculation unit 142, in the wavelength band $\gamma_i$ out of N wavelength bands is denoted as $\beta^M(\gamma_i)$. Each of Formulas expressed as Formula. 2 to Formula. 4 is an example of Formula representing a calculation method for calculating the second intermediate-optical-path-radiance $\beta^M(\gamma_i)$ in the wavelength band $\gamma_i$. Each of Formulas expressed as Formula. 2 to Formula. 4 is Formula based on a rule of thumb. The second intermediate-optical-path-radiance calculation unit 142 calculates the second intermediate-optical-path-radiance $\beta^M(\gamma_i)$, for example, by using any one of Formulas of Formula. 2 to Formula. 4.

$$\beta^M(\gamma_i) = X_1 I(\gamma_i) \gamma_i^{-X_2} \quad \text{[Formula. 2]}$$

A unit (dimension) of $\beta^M(\gamma_i)$ in Formula. 2 is W (watt)/steradian×(m (meter))$^{-3}$. A unit of $I(\gamma_i)$ is W/m$^{-3}$. A unit of $\gamma_i$ is m. $X_1$ and $X_2$ in Formula. 2 are parameters which express the atmosphere information having the following means respectively and which are determined based on experiences. Moreover, $X_1$ and $X_2$ have dimensions so that a part other than the term $I(\gamma_i)$ in a right side of Formula. 2 may have no dimension.

$X_1$: a parameter which expresses a degree of atmosphere turbidity such as a coefficient of atmosphere turbidity or the like $X_2$: a parameter, which expresses an inclination (a large value when there are many small size particles) in a size of particle included by the atmosphere, such as the angstrom index or the like $$\beta^M(\gamma_i) = X_3 I(\gamma_i)(1 - e^{-X_1 \gamma_i - X_2}) \quad \text{[Formula. 3]}$$

Units of $\beta^M(\gamma_i)$, $I(\gamma_i)$ and $\gamma_i$ in Formula. 3 are the same as the units in Formula. 2. $X_1$ to $X_3$ in Formula. 3 are parameters which express the atmosphere information having the following means respectively and which are determined based on experiences. Moreover, $X_1$ to $X_3$ have dimensions so that a part other than the term $I(\gamma_i)$ in a right side of Formula. 3 may have no dimension.

$X_1$ and $X_2$: the same as the parameters in Formula. 1 respectively $X_3$: a parameter (depending on a relation between a position of the sun and a position of a sensor) which expresses a ratio of scattered light $$\beta^M(\gamma_i) = X_3 I(\gamma_i)(1 - e^{-(X_1 \gamma_i - X_2 + X_4 \tau(\lambda))}) \quad \text{[Formula. 4]}$$

Units of $\beta^M(\gamma_i)$, $I(\gamma_i)$ and $\gamma_i$ in Formula. 4 are the same as the units in Formula. 2. and Formula. 3. $X_1$ to $X_4$ in Formula. 4 are parameters which express the atmosphere information having the following means respectively and which are determined based on experiences. Moreover, $X_1$ to $X_4$ have dimensions so that a part other than the term $I(\gamma_i)$ in a right side of Formula. 4 may have no dimension.

$X_1$ to $X_3$: the same as the parameters in Formula.3 respectively $X_4$: a parameter which expresses a degree of influence of the atmosphere transmittance on the optical-path-radiance The cost calculation unit 141 calculates a cost C by using the first intermediate-optical-path-radiance $\beta^D(\gamma_i)$ which is outputted by the first intermediate-optical-path-radiance calculation unit 12, and the second intermediate-optical-path-radiance $\beta^M(\gamma_i)$ which is calculated by the second intermediate-optical-path-radiance calculation unit 142. Here, the cost C is a value which indicates a degree of difference between the second intermediate-optical-path-radiance, and actual-optical-path-radiance at a time of observation. Formula. 5 is an example of Formula which expresses a cost C calculation method. The cost calculation unit 141 calculates the cost C, for example, by using a mathematical Formula shown in Formula. 5.

$$C = \sum_{i=1}^{N} (\beta^D(\gamma_i) - \beta^M(\gamma_i))^2 \quad \text{[Formula. 5]}$$

The cost minimization unit 143 sequentially updates values of M parameters to generate the atmosphere information $X_j$. When a value of the cost C calculated by the cost calculation unit 141 meets a predetermined condition, the cost minimization unit 143 outputs the final-optical-path-radiance and estimated atmosphere information. The final-optical-path-radiance outputted by the cost minimization unit 143 is a value, which makes the value of the cost C that is calculated by the cost calculation unit 141 minimum, out of the values of the second intermediate-optical-path-radiance which are calculated by the second intermediate-optical-path-radiance calculation unit 142. Moreover, the estimated atmosphere information is atmosphere information which is obtained when the cost calculated by the cost calculation unit 141 is minimized. The final-optical-path-radiance is a calculation value of the final-optical-path-radiance which is calculated at a time of observation. Moreover, the estimated atmosphere information is a value of the atmosphere information which is finally estimated at a time of observation.

In the following explanation, the final-optical-path-radiance, which is calculated by the cost minimization unit 143, in the wavelength band $\gamma_i$ out of N wavelength bands is denoted as $\beta^E(\gamma_i)$. Moreover, the estimated atmosphere information is denoted as $X^E_j$. Moreover, as intermediate parameters which are used in a process for calculating the final-optical-path-radiance $\beta^E(\gamma_i)$, the cost minimization unit 143 stores the minimum cost $C^m$ which is obtained at the present point of time, the atmosphere information $X^m_j$ which is obtained when the value of the cost is the minimum cost $C^m$, and the atmosphere information $X^b_j$ which is obtained at a previous time when sequentially updating M values of parameters. As initial values of the minimum cost $C^m$, the atmosphere information $X^m_j$ at the time of the minimum cost, and the atmosphere information $X_j$, the cost minimization unit 143 stores predetermined values.

The cost minimization unit 143 outputs the atmosphere information $X_j$ by sequentially updating the values of M parameters with, for example, the following method. Firstly, the cost minimization unit 143 outputs the stored initial value of the atmosphere information $X_j$. At every time when inputting the cost C, the cost minimization unit 143 carries out the following process, and outputs the atmosphere information $X_j$.

The cost minimization unit 143 compares the cost C and the minimum cost $C^m$. In the case that the cost C is smaller than the minimum cost $C^m$, the cost minimization unit 143 substitutes the cost C for the minimum cost $C^m$, and substitutes the atmosphere information $X_j$ for the atmosphere information $X^m_j$ which is obtained at the time of the minimum cost. The cost minimization unit 143 stores the updated minimum cost $C^m$ and the updated atmosphere information $X^m_j$ which is obtained at the time of the minimum cost. The cost minimization unit 143 substitutes a value which is obtained by adding a predetermined value to the parameter of the atmosphere information $X^b_j$, which is obtained at a previous time, for the parameter of the atmosphere information $X_j$, and outputs the substitution value. The cost minimization unit 143 substitutes the updated value of the atmosphere information $X_j$ for the atmosphere information $X^b_j$ which is obtained at a previous time, and stores the substitution value.

Moreover, the cost minimization unit 143 outputs the final optical path radiance $\beta^E(\gamma_i)$ and the estimated atmosphere information $X^E_j$ when the value of the cost C meets the predetermined condition with the following method. In the case that the value of the cost C is smaller than a predetermined value, the cost minimization unit 143 uses a mathematical Formula which is the same as the mathematical formula used when the second intermediate-optical-path-radiance calculation unit 142 calculates the second intermediate-optical-path-radiance $\beta^M(\gamma_i)$. For example, in the case that the second intermediate-optical-path-radiance calculation unit 142 calculates the second intermediate-optical-path-radiance $\beta^M(\gamma_i)$ by using Formula. 2, the cost minimization unit 143 works as follows.

The cost minimization unit 143 substitutes the value of atmosphere information $X^b_j$, which is obtained at a previous time, for the atmosphere information $X_j$. The cost minimization unit 143 calculates the second intermediate-optical-path-radiance $\beta^M(\gamma_i)$ by using Formula. 2. The cost minimization unit 143 substitutes the calculated value of the second intermediate-optical-path-radiance $\beta^M(\gamma_i)$ for the final-optical-path-radiance $\beta_E(\gamma_i)$. The cost minimization unit 143 substitutes the value of the atmosphere information $X^m_j$, which is obtained at the time of the minimum cost, for the estimated atmosphere information $X^E_j$. Then, the cost minimization unit 143 outputs the final optical path radiance $\beta^E(\gamma_i)$ and the estimated atmosphere information $X^E_j$. Similarly, in the case that the second intermediate-optical-path-radiance calculation unit 142 calculates the second intermediate-optical-path-radiance $\beta^M(\gamma_i)$ by using Formula. 3 or Formula. 4, also the cost minimization unit 143 calculates the second intermediate-optical-path-radiance $\beta^M(\gamma_i)$ by using Formula. 3 or Formula. 4.

Moreover, in the case of calculating the second intermediate-optical-path-radiance $\beta^M(\gamma_i)$, for example, by using Formula. 2, the cost minimization unit 143 works as follows. That is, the cost minimization unit 143 sequentially updates the value of the atmosphere information $X_j$, and outputs the updated value of the atmosphere information $X_j$ as shown in the following. Firstly, the cost minimization unit 143 outputs the initial value of the atmosphere information $X_j$. Hereinafter, at every time when inputting the cost C, the cost minimization unit 143 calculates the value of the atmosphere information $X_j$ by using Formula. 6 (matrix formula), and outputs the value of the atmosphere information $X_j$.

$$\begin{bmatrix} X_1 \\ X_2 \end{bmatrix} = \begin{bmatrix} X_1^b \\ X_2^b \end{bmatrix} - \alpha \begin{bmatrix} -2\sum_{i=1}^{N} I(\gamma_i)\gamma_i^{-X_2^b} \\ 2X_1^b \sum_{i=1}^{N} I(\gamma_i)(\log_e \gamma_i)\gamma_i^{-X_2^b} \end{bmatrix} \quad \text{[Formula. 6]}$$

The cost minimization unit 143 substitutes the value of the atmosphere information $X_j$ for the atmosphere information $X^b_j$ which is obtained at a previous time, and substitutes the value of cost C for a cost $C^b$ which is obtained at a previous time. The cost minimization unit 143 stores the atmosphere information $X^b_j$ and the cost $C^b$ whose values are changed and which are obtained at the previous time.

Moreover, in the case that the cost minimization unit 143 calculates, for example, the second intermediate-optical-path-radiance $\beta^M(\gamma_i)$ by using Formula. 2, by working as follows, the cost minimization unit 143 judges that the cost C meets the predetermined condition, and afterward outputs the final-optical-path-radiance $\beta^E(\gamma_i)$ and the estimated atmosphere information $X^E_j$. The cost minimization unit 143 compares a difference between the cost C and the cost $C^b$, which is obtained at the previous time, with a predetermined value. When the difference between the cost C and the cost $C^b$, which is obtained at the previous time, is smaller than the predetermined value, the cost minimization unit 143 works as follows.

The cost minimization unit 143 substitutes the value of the atmosphere information $X^b_j$, which is obtained at a previous time, for the atmosphere information $X_j$. The cost minimization unit 143 calculates the second intermediate-optical-path-radiance $\beta^M(\gamma_i)$ by using Formula. 2. The cost minimization unit 143 substitutes the calculated value of the second intermediate-optical-path-radiance $\beta^M(\gamma_i)$ for the final-optical-path-radiance $\beta^E(\gamma_i)$. The cost minimization unit 143 substitutes the value of the atmosphere information $X^m_j$, which is obtained at the time of the minimum cost, for the estimated atmosphere information $X^E_j$. Then, the cost minimization unit 143 outputs the final-optical-path-radiance $\beta^E(\gamma_i)$ and the estimated atmosphere information $X^E_j$.

The optical-path-radiance correction unit 15 corrects a component of the optical-path-radiance, which is included by the observation image, by using the observation image which the storage unit 11 stores, and the final-optical-path-radiance $\beta^E(\gamma_i)$, which the cost minimization unit 143 outputs, to generate an optical path radiance correction image. For example, the optical-path-radiance correction unit 15 works as follows.

The optical-path-radiance correction unit 15 reads the observation image, which is associated with the wavelength band $\gamma_i$ out of N wavelength bands, from the storage unit 11. The optical-path-radiance correction unit 15 carries out correction of subtracting the final-optical-path-radiance $\beta^E(\gamma_i)$, which the cost minimization unit 143 outputs, from the radiance value $L(\gamma_i)$ for all pixels composing the read observation image. That is, the corrected observation image is an image obtained by removing the component of the optical-path-radiance, which is calculated by the final-optical-path-radiance calculation unit 14, from the observation image which the storage unit 11 stores. The image is defined as the optical-path-radiance correction image. The optical-path-radiance correction unit 15 carries out the above-mentioned correction process to all of the observation images which are associated with N wavelength bands including the wavelength band $\gamma_i$.

The output unit 19 outputs the optical-path-radiance correction image which is generated by the optical-path-radiance correction unit 15, and the estimated atmosphere information $X^E_j$, which is outputted by the cost minimization unit 143, to the output device 6.

Figure 2:
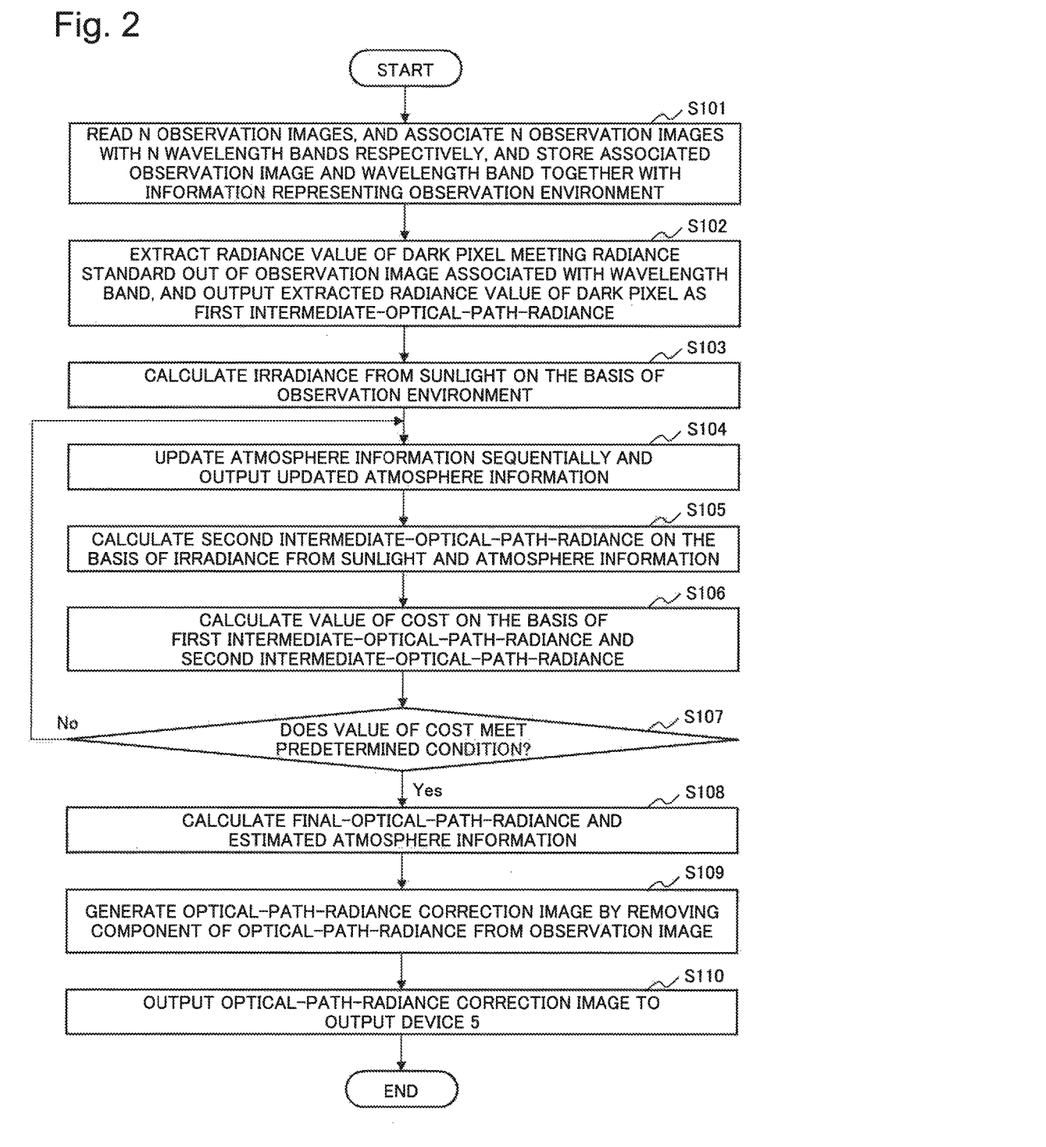
FIG. 2 is a flowchart showing an operation of the image information processing system according to the first example embodiment of the invention of the present application.

Next, with reference to a flowchart shown in FIG. 2, an operation (process) of the image information processing system 100 according to the present example embodiment will be explained in detail.

The storage unit 11 reads N observation images associated with N wavelength bands by which observation is carried out, and the information which expresses the observation environment existing at a time of observation from the image supply device 5. The storage unit 11 associates the read observation image with the wavelength band by which the observation image is observed, and stores the observation image and the wavelength band, which are associated, together with information which expresses an observation environment (Step S101). The first intermediate-optical-path-radiance calculation unit 12 extracts the radiance value of the dark pixel, which meets the radiance standard, out of all pixels of each of the observation images which are associated with the wavelength bands respectively, and outputs the extracted radiance values related to N wavelength bands as the first intermediate-optical-path-radiance (Step S102).

The irradiance calculation unit 13 calculates the irradiance from the sunlight on the basis of the information which expresses the observation environment (Step S103). At every time when the cost calculation unit 141 calculates a new cost, the cost minimization unit 143 sequentially updates the value of the atmosphere information, and outputs the updated value of the atmosphere information (Step S104). The second intermediate-optical-path-radiance calculation unit 142 calculates the second intermediate-optical-path-radiance on the basis of the irradiance from the sunlight which the irradiance calculation unit 13 calculates, and the atmosphere information which the cost minimization unit 143 outputs (step S105).

The cost calculation unit 141 calculates the cost on the basis of the first intermediate-optical-path-radiance which the first intermediate-optical-path-radiance calculation unit 12 outputs, and the second intermediate-optical-path-radiance which the second intermediate-optical-path-radiance calculation unit 142 calculates (Step S106).

In the case that the cost meets the predetermined condition (Yes in Step S107), the cost minimization unit 143 calculates the final-optical-path-radiance and the estimated atmosphere information (Step S108). In the case that the cost does not meet the predetermined condition (No in Step S107), the process returns to step S104.

The optical-path-radiance correction unit 15 removes the component of the optical-path-radiance, which is included by the observation image, by using the observation image and the final-optical-path-radiance to generate the optical-path-radiance correction image (Step S109). The output unit 19 outputs the optical-path-radiance correction image, which the optical-path-radiance correction unit 15 generates, to the output device 6 (step S110), and then the whole process has been finished.

The image information processing system 100 according to the present example embodiment can calculate the optical-path-radiance with a high degree of accuracy even in the wavelength band in which the surface reflectance of the dark area in the image representing the observed ground surface area cannot be considered to be 0. The reason is that the final-optical-path-radiance calculation unit 14 calculates the cost, which indicates the degree of difference between the second intermediate-optical-path-radiance and the actual-optical-path-radiance, by using the first intermediate-optical-path-radiance which is calculated by the first intermediate-optical-path-radiance calculation unit 12, and the second intermediate-optical-path-radiance which is calculated by the second intermediate-optical-path-radiance calculation unit 142, and outputs the second intermediate-optical-path-radiance, which is calculated at the time when the cost becomes minimum, as the final-optical-path-radiance.

An effect which is obtained by the image information processing system 100 according to the present example embodiment will be explained in the following in detail. In the case of the general image information processing device 4 shown in FIG. 6, it is impossible to calculate the optical-path-radiance with a high degree of accuracy in the wavelength band in which the surface reflectance of the area, that is corresponding to the pixel having small radiance, out of the ground surface area observed as the image cannot be considered to be 0. That is, by the dark pixel assumption, it is difficult to calculate the actual-optical-path-radiance at a time of observation with a high degree of accuracy.

In contrast, in the case of the image information processing device 1 according to the present example embodiment, the first intermediate-optical-path-radiance calculation unit 12 extracts the radiance value of the dark pixel, which meets the radiance standard, from the observation image which is associated with the wavelength band, and outputs the extracted radiance value as the first intermediate-optical-path-radiance. The second intermediate-optical-path-radiance calculation unit 142 repeatedly calculates the second intermediate-optical-path-radiance with updating the irradiance from the sunlight which is calculated by the irradiance calculation unit 13, and the atmosphere information which is calculated by the cost minimization unit 143. Then, as the final-optical-path-radiance, the final-optical-path-radiance calculation unit 14 outputs the second intermediate-optical-path-radiance obtained when the cost, which is calculated on the basis of the first intermediate-optical-path-radiance and the second intermediate-optical-path-radiance, is minimized. Accordingly, the image information processing device 1 according to the present example embodiment can calculate the optical-path-radiance with a high degree of accuracy even in the wavelength band in which the surface reflectance of the dark area in the image representing the observed ground surface area cannot be considered to be 0.

Moreover, the final-optical-path-radiance calculation unit 14 of the image information processing device 1 according to the present application example embodiment outputs the estimated atmosphere information together with the final-optical-path-radiance through the output unit 19. The estimated atmosphere information is information which indicates the state of the atmosphere existing at a time of observation. Therefore, the image information processing device 1 according to the present example embodiment can obtain the atmosphere information which can be used effectively as weather information.

<Second Example Embodiment>

Figure 3:
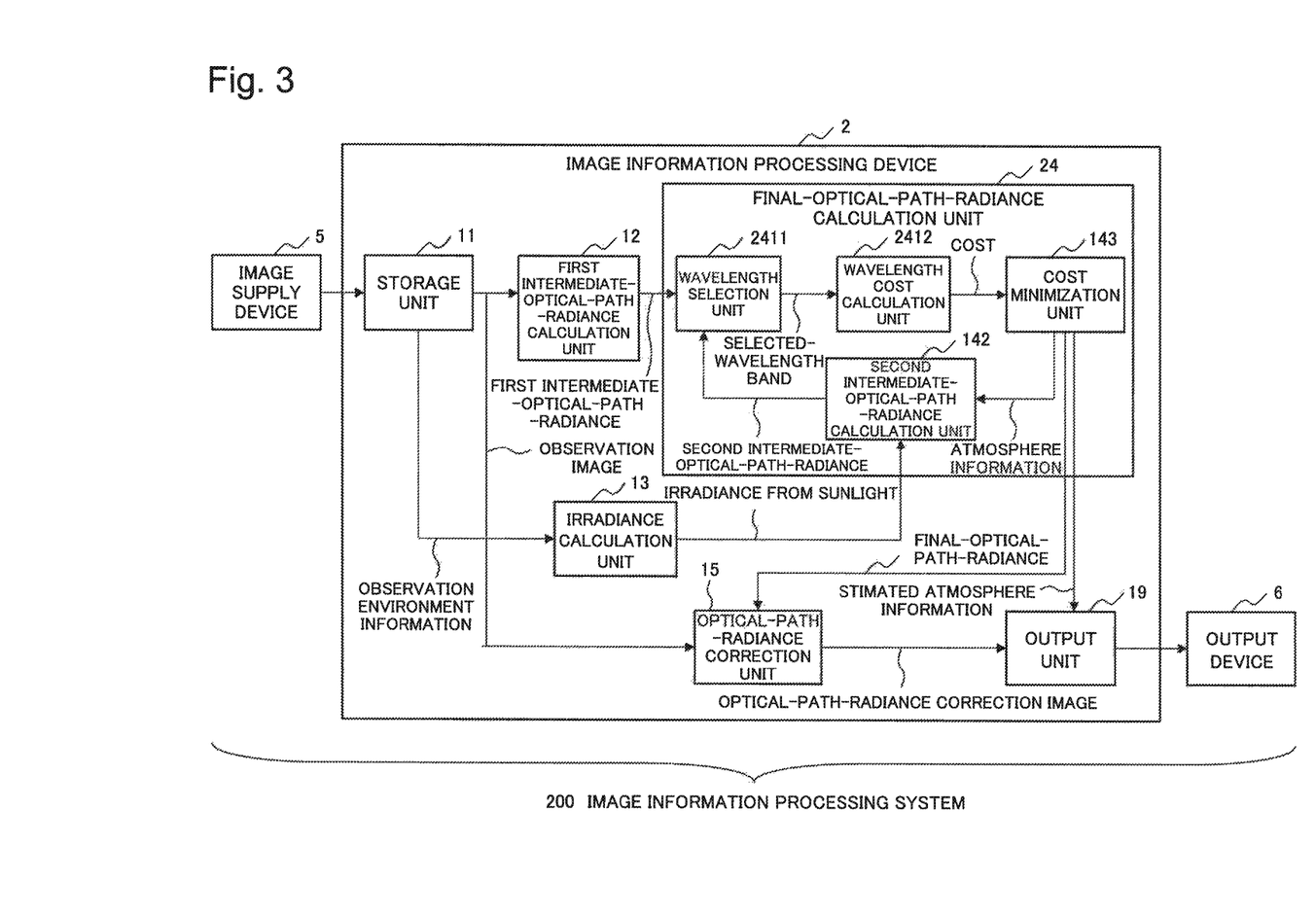
FIG. 3 is a block diagram showing a configuration of an image information processing system according to a second example embodiment of the invention of the present application.

FIG. 3 is a block diagram which conceptually shows a configuration of an image information processing system 200 according to a second example embodiment. In the following description, explanation is omitted by assigning a code, which is the same as the code used in the first example embodiment, to a component which works identically to the component of the first example embodiment.

The image information processing system 200 according to the present example embodiment includes an image information processing device 2, the image supply device 5 and the output device 6 as a main component.

The image information processing device 2 includes the storage unit 11, the first intermediate-optical-path-radiance calculation unit 12, the irradiance calculation unit 13, a final-optical-path-radiance calculation unit 24, the optical-path-radiance correction unit 15, and the output unit 19. The final-optical-path-radiance calculation unit 24 may be realized by an electronic circuit in some cases, and may be realized by a computer program and a processor, which works according to the computer program, in the other cases.

The final-optical-path-radiance calculation unit 24 includes a wavelength selection unit 2411, a wavelength cost calculation unit 2412, the second intermediate-optical-path-radiance calculation unit 142 and the cost minimization unit 143.

The final-optical-path-radiance calculation unit 24 calculates the final-optical-path-radiance $\beta^E(\gamma_i)$ (i is an integer of any one of 1 to N) and the estimated atmosphere information $X^E_j$, by using the first intermediate-optical-path-radiance $\beta^D(\gamma_i)$ which the first intermediate-optical-path-radiance calculation unit 12 outputs, and the irradiance $I(\gamma_i)$ from the sunlight which the irradiance calculation unit 13 calculates. The final-optical-path-radiance calculation unit 24 selects the wavelength band γi out of N wavelength bands on the basis of a predetermined standard, and calculates a value in the selected wavelength band, and a value in the not-selected wavelength band with different methods respectively, and afterward calculates addition of two values. Then, the final-optical-path-radiance calculation unit 24 makes the result of addition a cost. Moreover, the final-optical-path-radiance calculation unit 24 outputs the second intermediate-optical-path-radiance, which is obtained when the cost meets a predetermined condition, as the final-optical-path-radiance. The final-optical-path-radiance calculation unit 24 outputs the atmosphere information, which is obtained when the cost is minimized, as the estimated atmosphere information $X^E_j$.

The wavelength selection unit 2411 selects 1 or more wavelength bands from N observation wavelength bands by using the first intermediate-optical-path-radiance which the first intermediate-optical-path-radiance calculation unit 12 outputs, and the second intermediate-optical-path-radiance which the second intermediate-optical-path-radiance calculation unit 142 calculates, and outputs the selected wavelength band. Number of the wavelength bands which the wavelength selection unit 2411 selects is P which is any one of 1 to (N−1). In the following explanation, the wavelength band which the wavelength selection unit 2411 selects is denoted as a selected wavelength band $\gamma_j$ (j is an integer of any one of $s_1$ to $s_P$).

For example, the wavelength selection unit 2411 compares the first intermediate-optical-path-radiance $\beta^D(\gamma_i)$ and the second intermediate-optical-path-radiance $\beta^M(\gamma_i)$ in turn for each wavelength band $\gamma_i$ out of N wavelength bands. In the case that the first intermediate-optical-path-radiance $\beta^D(\gamma_i)$ is higher (larger) than the second intermediate-optical-path-radiance $\beta^M(\gamma_i)$, the wavelength selection unit 2411 selects the wavelength band $\gamma_i$ and stores the wavelength band $\gamma_i$ as the selected wavelength band $\gamma_j$. At every time when the wavelength selection unit 2411 stores the selected wavelength band $\gamma_j$, the wavelength selection unit 2411 updates a value of j, and stores $\gamma s_1$ to $\gamma s_P$ in turn.

The wavelength cost calculation unit 2412 calculates the cost C by using the first intermediate-optical-path-radiance $\beta^D(\gamma_i)$ which the first intermediate-optical-path-radiance calculation unit 12 outputs, the second intermediate-optical-path-radiance $\beta^M(\gamma_i)$ which the second intermediate-optical-path-radiance calculation unit 142 calculates, and the wavelength band $\gamma_i$ which the wavelength selection unit 2411 selects. For example, the wavelength cost calculation unit 2412 stores a predetermined value of a selected-wavelength cost coefficient A and a predetermined value of a not-selected-wavelength cost coefficient B. The selected-wavelength cost coefficient A is a coefficient representing a degree of influence of the first intermediate-optical-path-radiance on calculation of the final-optical-path-radiance in the wavelength band in which the dark pixel assumption is not met. The not-selected-wavelength cost coefficient B is a coefficient representing a degree of influence of the first intermediate-optical-path-radiance on calculation of the final-optical-path-radiance in the wavelength band in which the dark pixel assumption is met. The predetermined value of the selected-wavelength cost coefficient A is set to be smaller than the predetermined value of the not-selected-wavelength cost coefficient B. That is, the wavelength cost calculation unit 2412 gives weight, which is higher (larger) than weight of the wavelength band selected by the wavelength selection unit 2411, to the wavelength band not selected by the wavelength selection unit 2411, and calculates the cost C.

The wavelength cost calculation unit 2412 makes the wavelength band other than the selected wavelength band $\gamma_j$ out of N wavelength bands a not-selected wavelength band $\gamma_k$ (k is an integer of any one of $t_1$ to $t_{(N-P)}$). The wavelength cost calculation unit 2412 calculates the cost C by using Formula. 7. Here, a mark '·' in Formula. 7 indicates an operator of multiplication.

$$C = \sum_{j=s_1}^{s_P} A \cdot (\beta^D(\gamma_j) - \beta^M(\gamma_j))^2 + \sum_{k=t_1}^{t_{(N-P)}} B \cdot (\beta^D(\gamma_k) - \beta^M(\gamma_j))^2 \qquad \text{[Formula. 7]}$$

Similarly to the first example embodiment, the image information processing device 200 according to the present example embodiment can calculate the optical-path-radiance with a high degree of accuracy even in the wavelength band in which the surface reflectance of the dark area in the image representing the observed ground surface area cannot be considered to be 0. The reason is that the final-optical-path-radiance calculation unit 24 calculates the cost, which indicates the degree of difference between the second-intermediate-optical-path-radiance and the actual-optical-path-radiance, by using the first intermediate-optical-path-radiance which is calculated by the first intermediate-optical-path-radiance calculation unit 12, and the second intermediate-optical-path-radiance which is calculated by the second intermediate-optical-path-radiance calculation unit 142, and outputs the second intermediate-optical-path-radiance, which is obtained at the time when the cost is minimized, as the final-optical-path-radiance.

The predetermined value of the selected-wavelength cost coefficient A, which is stored by the wavelength cost calculation unit 2412, is set to be smaller than the predetermined value of the not-selected-wavelength cost coefficient B. Therefore, the image information processing device 2 according to the present example embodiment reduces influence of the estimation error, that relates to estimation of the first intermediate-optical-path-radiance and that is generated in the wavelength band in which the dark pixel assumption is not met, on calculation of the final-optical-path-radiance.

As a result, the image information processing device 2 according to the present example embodiment can calculate the optical-path-radiance with a higher degree of accuracy in comparison with the first example embodiment.

<Third Example Embodiment>

Figure 4:
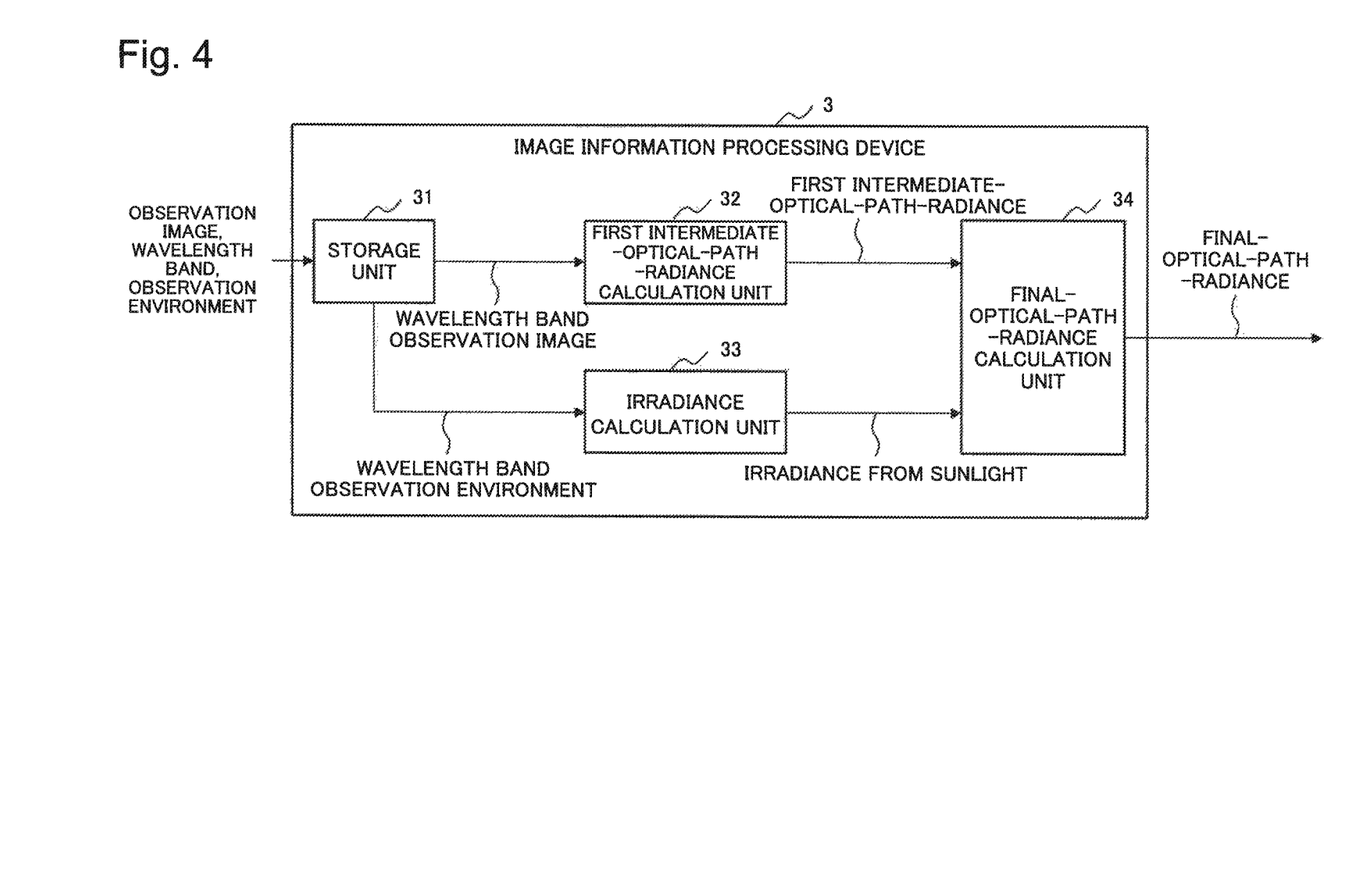
FIG. 4 is a block diagram showing a configuration of an image information processing system according to a third example embodiment of the invention of the present application.

FIG. 4 is a block diagram which conceptually shows a configuration of an image information processing device 3 according to a third example embodiment.

The image information processing device 3 according to the present example embodiment includes a storage unit 31, a first intermediate-optical-path-radiance calculation unit 32, an irradiance calculation unit 33 and a final-optical-path-radiance calculation unit 34.

In the storage unit 31, observation images representing results of observing electromagnetic waves of a plurality of different wavelength bands reflected from the ground surface, information representing the wavelength bands, and information representing an observation environment existing at a time when the electromagnetic waves are observed are associated and stored.

For each of the wavelength band, the first intermediate-optical-path-radiance calculation unit 32 calculates radiance of the dark pixel, which meets the radiance standard, out of pixels composing the associated observation image which is associated with the wavelength band, as a first intermediate-optical-path-radiance.

The irradiance calculation unit 33 calculates, for each of the wavelength band, the irradiance from the sunlight on the basis of the information representing the observation environment.

The final-optical-path-radiance calculation unit 34 calculates, for each of the wavelength band, a final-optical-path-radiance on the basis of the irradiance and the first intermediate-optical-path-radiance.

The image information processing device 3 according to the present example embodiment can calculate the optical-path-radiance with a high degree of accuracy even in the wavelength band in which the surface reflectance of the dark area in the image representing the observed ground surface area cannot be considered to be 0. The reason is that the final-optical-path-radiance calculation unit 34 calculates the final-optical-path-radiance, whose value is near to a value of the actual-optical-path-radiance, for each wavelength band by using the first intermediate-optical-path-radiance which is calculated by the first intermediate-optical-path-radiance calculation unit 32, and the irradiance from the sunlight which is calculated by the irradiance calculation unit 33.

<Example of Hardware Configuration>

Each unit shown in FIG. 1, FIG. 3 and FIG. 4 according to each example embodiment can be realized by dedicated HW (HardWare) (electronic circuit).

Moreover, at least, each of the first intermediate-optical-path-radiance calculation units 12 and 32, the irradiance calculation units 13 and 33, and the final-optical-path-radiance calculation units 14, 24 and 34 can be considered to be a function (process) unit (software module) of a software program. However, division into each unit shown in each drawing is a configuration determined temporarily for convenience of explanation, and various configurations can be conceived at a time of implementation. An example of a hardware environment in this case will be explained in the following with reference to FIG. 7.

Figure 7:
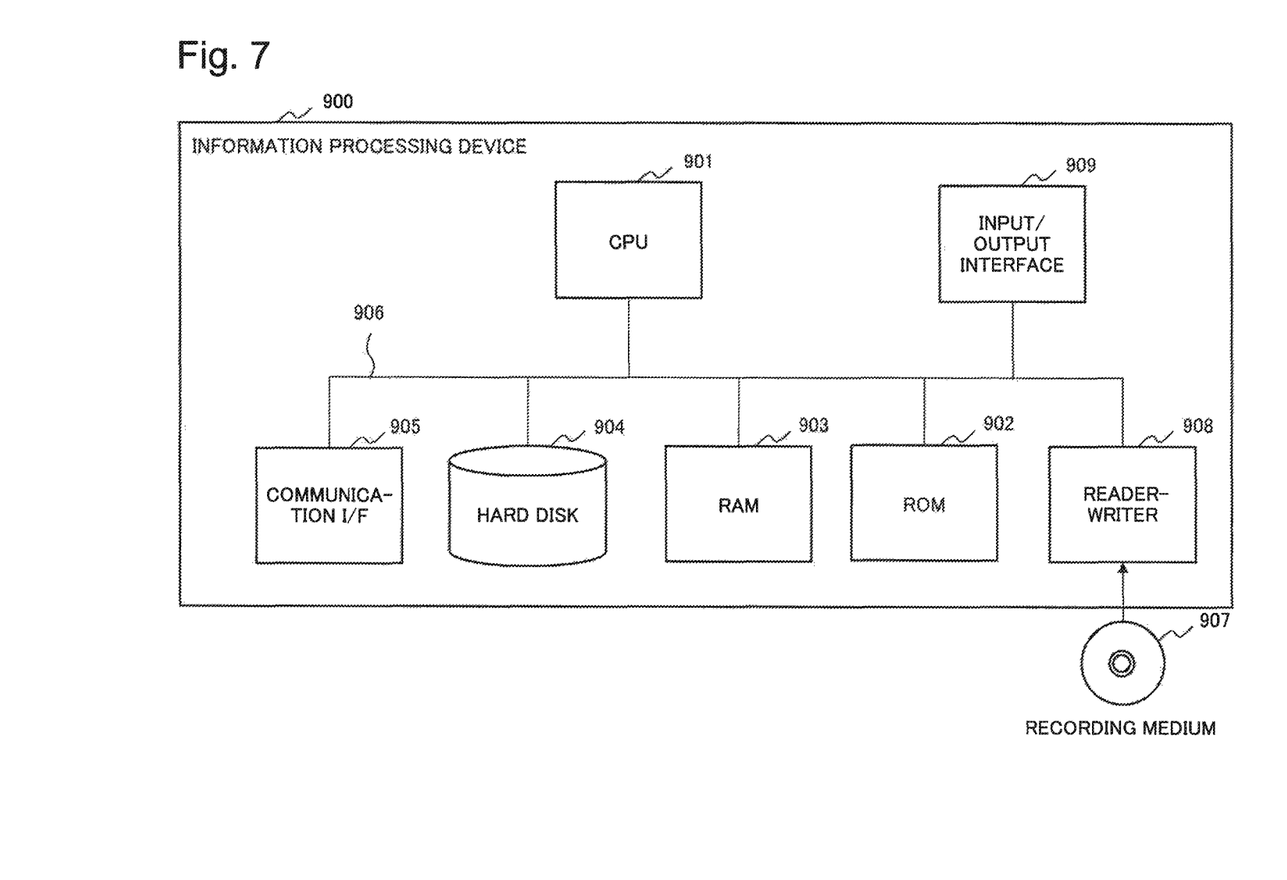
FIG. 7 is a block diagram showing a configuration of an information processing device which can carry out the image information processing device according to each example embodiment of the invention of the present application.

FIG. 7 is a diagram for exemplifying and explaining a configuration of an information processing device 900 (computer) which can carry out the image information processing device according to the example embodiment of the present invention. That is, FIG. 7 is the configuration of the computer (information processing device) which can realize the image information processing devices shown in FIG. 1, FIG. 3 and FIG. 4, and shows the hardware environment which can realize each function in the above-mentioned example embodiment.

The information processing device 900 shown in FIG. 7 includes components shown in the following.

CPU (Central_Processing_Unit) 901

ROM (Read_Only_Memory) 902

RAM (Random_Access_Memory) 903

Hard disk (storage device) 904

Communication interface 905 communicating with an external device

Bus 906 (communication line),

Reader-writer 908 which can read and write data stored by a recording medium 907 such as CD-ROM (Compact_Disc_Read_Only_Memory) or the like Input-output interface 909

The information processing device 900 is a general computer in which these components are connected each other through the bus 906.

According to the present invention which has been explained by using the above-mentioned example embodiments as examples, a computer program, which can realize the following functions, is supplied to the information processing device 900 shown in FIG. 7. The functions are functions of the first intermediate optical path radiance calculation units 12 and 32, the irradiance calculation units 13 and 33, and the final intermediate optical path radiance calculation units 14, 24 and 34 in the block diagrams (FIG. 1, FIG. 3 and FIG. 4) which are referred to in explanation of the example embodiment, or functions of the flowchart (FIG. 2). The present invention is achieved by reading the computer program, and supplying CPU 901, which is the hardware, with the computer program, and interpreting the computer program, and then carrying out the computer program. Also, the computer program which is supplied to the device may be stored in a volatile storage device (RAM 903) which is capable of reading and writing, or a non-volatile storage device such as the hard disk 904 or the like.

Moreover, in the above-mentioned case, a procedure which is general at the present time is applicable to a method for supplying the hardware with the computer program. As the procedure, for example, a method of installation in the device through the various recording media 907 such as CD-ROM or the like, or a method of down-loading through a communication circuit such as The Internet or the like is exemplified. Moreover, in this case, it is conceivable that the present invention is made from codes which compose the computer program, or from the recording medium 907 which stores the codes.

While the invention has been particularly shown and described with reference to example embodiments thereof, the invention is not limited to these embodiments. It will be understood by those of ordinary skill in the art that various changes in form and details may be made therein without departing from the spirit and scope of the present invention as defined by the claims.

This application is based upon and claims the benefit of priority from Japanese patent application No. 2014-257039, filed on Dec. 19, 2014, the disclosure of which is incorporated herein in its entirety by reference.

INDUSTRIAL APPLICABILITY

The present invention is available for farming support and the resources exploration which are based on the result of measuring the ground surface from the height.

REFERENCE SIGHS LIST 1 image information processing device
11 storage unit
12 first intermediate-optical-path-radiance calculation unit
13 irradiance calculation unit
14 final-optical-path-radiance calculation unit
141 cost calculation unit
142 second intermediate-optical-path-radiance calculation unit
143 cost minimization unit
15 optical-path-radiance correction unit
19 output unit
5 image supply device
6 output device
100 image information processing system
2 image information processing device
24 final-optical-path-radiance calculation unit
2411 wavelength selection unit
2412 wavelength cost calculation unit
200 image information processing system
3 image information processing device
31 storage unit
32 first intermediate-optical-path-radiance calculation unit
33 irradiance calculation unit
34 final-optical-path-radiance calculation unit
4 image information processing device
41 image reading unit
42 dark pixel identification unit
43 sensor parameter storage unit
44 atmosphere propagation correction unit
900 information processing device
901 CPU
902 ROM
903 RAM
904 hard disk (storage unit)
905 communication interface
906 bus
907 recording medium
908 reader-writer
909 Input-output interface

What is claimed is:

1. An image information processing device comprising:
a storage unit configured to store information, in which observation images representing results of observing electromagnetic waves of a plurality of different wavelength bands reflected from a ground surface, information representing the wavelength bands, and information representing an observation environment, which the electromagnetic waves are observed, are associated;
a first intermediate-optical-path-radiance calculation unit configured to calculate, for each of the wavelength band, radiance of a dark pixel meeting a radiance standard from among pixels composing the observation image, which is associated with the wavelength band, as a first intermediate-optical-path-radiance;
an irradiance calculation unit configured to calculate, for each of the wavelength band, irradiance from sunlight on the basis of the information representing the observation environment; and
a final-optical-path-radiance calculation unit configured to calculate, for each of the wavelength band, a final-optical-path-radiance on the basis of the irradiance and the first intermediate-optical-path-radiance.

2. The image information processing device according to claim 1, wherein
the final-optical-path-radiance calculation unit includes:
a cost minimization unit configured to sequentially generate atmosphere information on a state of the atmosphere by updating a value(s) of a variable(s) representing the atmosphere information;
a second intermediate-optical-path-radiance calculation unit configured to calculate a second intermediate-optical-path-radiance on the basis of the atmosphere information and the irradiance at every time when the cost minimization unit generates the atmosphere information; and
a cost calculation unit configured to calculate a value of a cost indicating a degree of difference between the second intermediate-optical-path-radiance and actual-optical-path-radiance which is a result of observing the electromagnetic wave, on the basis of the first and the second intermediate-optical-path-radiance, wherein
the cost minimization unit calculates the second intermediate-optical-path-radiance, when the value of the cost meets a predetermined condition, as the final-optical-path-radiance.

3. The image information processing device according to claim 2, wherein
the cost minimization unit calculates the second intermediate-optical-path-radiance, which is calculated when the value of cost is minimized, as the final-optical-path-radiance.

4. The image information processing device according to claim 2, wherein
the cost minimization unit outputs the atmosphere information, which is generated when the value of the cost meets the predetermined condition, to an outside.

5. The image information processing device according to claim 1, wherein
the final-optical-path-radiance calculation unit, comprising:
a cost minimization unit configured to sequentially generate atmosphere information on a state of the atmosphere by updating the value(s) of the variable(s) representing the atmosphere information;
a second intermediate-optical-path-radiance calculation unit configured to calculate a second intermediate-optical-path-radiance on the basis of the atmosphere information and the irradiance at every time when the cost minimization unit generates the atmosphere information;
a wavelength selection unit configured to select one or more wavelength bands out of a plurality of wavelength bands on the basis of the first and the second intermediate-optical-path-radiance; and
a wavelength cost calculation unit configured to calculate a value of a cost indicating a degree of difference between the second intermediate-optical-path-radiance, and actual-optical-path-radiance which is a result of observing the electromagnetic wave, on the basis of information indicating the first and the second intermediate-optical-path-radiance and the wavelength band which is selected by the wavelength selection unit, and wherein the cost minimization unit calculates the second intermediate-optical-path-radiance, when the value of the cost meets a predetermined condition, as the final-optical-path-radiance.

6. The image information processing device according to claim 5, wherein
the wavelength selection unit selects the wavelength band in which the first intermediate-optical-path-radiance is higher than the second intermediate-optical-path-radiance, and wherein
the wavelength cost calculation unit calculates the value of the cost giving more weight to the wavelength band which is not selected by the wavelength selection unit than the wavelength band which is selected by the wavelength selection unit.

7. The image information processing device according to claim 1, further comprising:
an optical-path-radiance correction unit configured to generate, for each the wavelength band, an optical-path-radiance correction image by removing a component which is indicated by the final-optical-path-radiance from the observation image.

8. An image information processing system, comprising:
an image information processing device including;
a storage unit configured to store information, in which observation images representing results of observing electromagnetic waves of a plurality of different wavelength bands reflected from a ground surface, information representing the wavelength bands, and information representing an observation environment, which the electromagnetic waves are observed, are associated;
a first intermediate-optical-path-radiance calculation unit configured to calculate, for each of the wavelength band, radiance of a dark pixel meeting a radiance standard from among pixels composing the observation image, which is associated with the wavelength band, as a first intermediate-optical-path-radiance;
an irradiance calculation unit configured to calculate, for each of the wavelength band, irradiance from sunlight on the basis of the information representing the observation environment; and
a final-optical-path-radiance calculation unit configured to calculate, for each of the wavelength band, a final-optical-path-radiance on the basis of the irradiance and the first intermediate-optical-path-radiance; and
an image supply device that is connected with the image information processing device so as to be able to communicate, and associates the observation image with the wavelength band in which the observation image is observed, and the information representing the observation environment, and inputs the observation image into the image information processing device.

9. An image information processing method comprising:
in a case that observation images representing results of observing electromagnetic waves of a plurality of different wavelength bands reflected from a ground surface, information representing the wavelength bands, and information representing an observation environment, which the electromagnetic waves are observed, are associated and stored in a storage unit, by an information processing device:
calculating, for each of the wavelength band, radiance of a dark pixel meeting a radiance standard from among pixels composing the observation image which is associated with the wavelength band, as a first intermediate-optical-path-radiance;
calculating, for each of the wavelength band, irradiance from sunlight on the basis of the information representing the observation environment; and
calculating, for each of the wavelength band, a final-optical-path-radiance on the basis of the irradiance and the first intermediate-optical-path-radiance.

10. A non-transitory computer readable recording medium storing an image information processing program for making a computer, which is capable of accessing a storage unit in which observation images representing results of observing electromagnetic waves of a plurality of different wavelength bands reflected from a ground surface, information representing the wavelength bands, and information representing an observation environment, which the electromagnetic waves are observed, are associated and stored, carry out following processing:
an intermediate-optical-path-radiance calculation processing of calculating, for each of the wavelength band, radiance of a dark pixel meeting a radiance standard from among pixels composing the observation image which is associated with the wavelength band, as a first intermediate-optical-path-radiance;
an irradiance calculation processing of calculating, for each of the wavelength band, irradiance from sunlight on the basis of the information representing the observation environment; and
a final-optical-path-radiance calculation processing of calculating, for each of the wavelength band, a final-optical-path-radiance on the basis of the irradiance and the first intermediate-optical-path-radiance.

* * * * *